United States Patent [19]

Rei et al.

[11] Patent Number: 5,405,610
[45] Date of Patent: Apr. 11, 1995

[54] PHOSPHITES AS CONSOLVENTS FOR BIOCIDE/PLASTICIZER SOLUTIONS CONTAINING HIGH ANTIMICROBIAL CONCENTRATIONS

[75] Inventors: Nuno M. Rei, Boxford; Roger G. Hamel, Methuen, both of Mass.

[73] Assignee: Morton International, Inc., Chicago, Ill.

[21] Appl. No.: 102,671

[22] Filed: Aug. 5, 1993

Related U.S. Application Data

[63] Continuation of Ser. No. 906,977, Jun. 30, 1992, abandoned.

[51] Int. Cl.$^6$ .................. A01N 25/32; A01N 59/22
[52] U.S. Cl. .......................... 424/405; 424/406; 424/621
[58] Field of Search ............................ 424/405

[56] References Cited

U.S. PATENT DOCUMENTS

| | | | |
|---|---|---|---|
| Re. 29,409 | 9/1977 | Yaeger | 424/78 |
| 3,288,674 | 11/1966 | Yeager | 167/42 |
| 3,360,431 | 12/1967 | Yaeger | 167/30 |
| 3,689,449 | 9/1972 | Yaeger et al. | 260/33.4 |
| 4,049,822 | 9/1977 | Rei et al. | 424/297 |
| 4,663,077 | 5/1987 | Rei et al. | 252/364 |
| 4,891,391 | 1/1990 | McEntee | 523/122 |

*Primary Examiner*—Thurman K. Page
*Assistant Examiner*—Neil Levy
*Attorney, Agent, or Firm*—Mark F. LaMarre; Robert M. Didrick; Gerald K. White

[57] ABSTRACT

A microbicidal solution for resin compositions including a phenoxarsine compound and a liquid plasticizer with an organophosphite or organophosphonate cosolvent. Further, this invention relates to a microbicidal compositions comprising a liquid plasticizer and a microbicidal compound dissolved in an alkyl, aryl, or alkyl-aryl phosphite; or an alkyl, aryl, or alkyl-aryl phosphonate cosolvent.

14 Claims, No Drawings

PHOSPHITES AS CONSOLVENTS FOR BIOCIDE/PLASTICIZER SOLUTIONS CONTAINING HIGH ANTIMICROBIAL CONCENTRATIONS

This is a continuation of application Ser. No. 07/906,977, filed on Jun. 30, 1992, now abandoned.

This invention relates to microbicidal compositions containing a phenoxarsine compound and more particularly to compositions comprising a liquid plasticizer and a microbicidal compound dissolved in an organophosphite or organophosphonate cosolvent. Further, this invention relates to a microbicidal compositions comprising a liquid plasticizer and a microbicidal compound dissolved in an alkyl, aryl, or alkyl-aryl phosphite; or an alkyl, aryl, or alkyl-aryl phosphonate cosolvent.

It is presently common practice to protect polymer or plastic compositions from microbial, e.g. bacterial or fungal, attack by incorporating a microbicidal composition in the polymer or plastic. The resulting polymer compositions prevent the deterioration of articles formed from the polymer composition due to microbiological attack on the plasticizers or other polymer additives which are normally incorporated into the polymer composition to impart desirable physical properties to the article, to facilitate forming of the article, or to act as polymer processing aids.

Many of the available microbicidal materials are fine powders. In order to eliminate the hazards associated with the uncontrolled entry of the powdered microbicidal materials into the manufacturing environment and to incorporate them homogeneously into the polymer resin compositions, it is desirable first to mix them with a liquid which solubilizes or disperses the material uniformly, and then mix the liquid composition with the resin. Unfortunately, the solubility of many of the microbicidally active materials in the common plasticizers is quite low. Therefore, it is either difficult to incorporate a sufficiently high concentration of the microbicidal material with the polymer resin or, if sufficiently high concentrations of the active material can be incorporated in to the polymer resin, an undesirably high concentration of the plasticizer also must be incorporated into the polymer resin with the resultant deterioration of the desirable characteristics of the resin composition.

Attempts to solve these problems have met with varying, often limited, success. For example, as disclosed in U.S. Pat. Nos. 3,689,449 issued Sep. 5, 1972 to Yeager et al. and 3,288,674, issued Nov. 29, 1966 to Yeager (reissued on Sep. 20, 1977 as Re. 29,409) it has been proposed to form solutions of microbicidal phenoxarsine compounds and a solvent having a labile hydrogen, preferably nonyl phenol and $C_5$-$C_{12}$ alcohols, for subsequent incorporation into resin compositions. Unfortunately, the solubility of the phenoxarsines in nonyl phenol/plasticizer mixtures is limited to lower concentrations of phenoxarsines. Thus, the maximum amount of phenoxarsine disclosed as being incorporated into a plasticizer composition is only 2.5% by weight (based on the total weight of phenoxarsine, nonyl phenol, and plasticizer).

U.S. Pat. No. 3,360,431 issued Dec. 26, 1967 to Yeager discloses the use of labile hydrogen-containing solvents, preferably nonyl phenol, to dissolve microbicidally active arsenobenzene compound for subsequent addition to resin compositions.

U.S. Pat. No. 4,663,077 issued May 5, 1987 to Rei et al., which patent is assigned to the assignee of the present invention, discloses the use of aryl alkanols as cosolvents for microbicidal compounds and carriers such as plasticizers and/or other processing aids, the resulting compositions being subsequently incorporated into polymer resin compositions.

U.S. Pat. No. 4,049,822 issued Sep. 20, 1977 to Rei et al., which patent is assigned to the assignee of the present invention, discloses the use of glycyl phosphite and glycyl phosphonates as cosolvents for microbicidal compounds above 20% by weight of the composition and up to 2% by weight of the composition containing plasticizers. The Rei patent erroneously discloses a composition containing 40 wt. % of the microbicide OBPA, 20 wt. % Poly (dipropylene glycylphenyl) phosphite, 20 wt. % diisooctyl phosphite, and 20 wt. % dioctyl phthalate, a plasticizer, in a table of microbicides and cosolvents. This erroneous example "L" is the only plasticizer containing composition which appears in this table. This composition has been shown through later tests to be unstable.

SUMMARY OF THE INVENTION

It is an object of this invention to provide microbicidal compositions which contain high concentrations of a microbicidal material. This would permit incorporating the microbicidal composition at the desired concentration in a resin while controlling the concentration of cosolvent and plasticizer within relatively low levels in order to minimize their effect on the overall properties of the resin composition. Also, it is an object of this invention to provide microbicidal compositions which can be incorporated into resins and which also contain the usual resin modifiers such as antioxidants, heat stabilizers, UV stabilizers and plasticizers without adversely affecting the microbicidal activity. This would permit incorporation of the usual resin additives with the resin in a single step.

In accordance with the present invention there are provided homogeneous, stable liquid microbicidal composition comprising a plasticizer, a microbicidal compound, and a cosolvent, wherein said microbicidal compound is present in the microbicidal composition from about 2.5%, based on the total weight of the composition, to an amount such that the microbicidal compound is stable in said microbicidal composition, wherein said microbicidal compound is selected from the group consisting of phenoxarsines and phenarsazines, said microbicidal compound being present as the solute in an organophosphite cosolvent or organophosphonate cosolvent such that the weight ratio of the organophosphite or organophosphonate cosolvent to microbicidal compound is from about 1/1 to about 5/1.

Further, In accordance with the present invention there are provided homogeneous, stable liquid compositions comprising a plasticizer, and from about 2.5% to about 15% by weight, based on the total weight of the microbicide, cosolvent, and plasticizer, of a microbicidal compound selected from the group consisting of phenoxarsines and phenarsazines, said microbicidal compound being present as the solute in an organophosphite or organophosphonate, as a cosolvent, such that the weight ratio of the organophosphite or organophosphonate solvent to microbicidal compound is from about 1/1 to about 5/1, and preferably from about 3/1 to about 5/1, to provide a lower toxicity microbicidal solution. Organophosphites and organophosphonates are herein defined as organic compounds containing phosphite or phosphonate linkages.

Further, this invention also includes stable, liquid compositions comprising a plasticizer, and from more than 2.5% to about 15% by weight, based on the total weight of the composition, of a microbicidal compound selected from the group consisting of phenoxarsines and phenarsazines, said microbicidal compound being present as the solute in an alkyl, aryl, alkyl-aryl, or thiophosphite; or an alkyl, aryl, alkyl-aryl or glycol, phosphonate, as a cosolvent, such that the weight ratio of the phosphite or phosphonate solvents to microbicidal compound is from about 1/1 to about 5/1, and preferably from about 3/1 to about 5/1. This invention also includes stable liquid compositions comprising a plasticizer, and from about 2.5% to about 10% by weight, based on the total weight of the composition, of a microbicidal compound being present as the solute in a glycol phosphite or glycol phosphate.

DETAILED DESCRIPTION OF THE INVENTION

The present invention is specifically directed to applications in which the microbicidal compound is not sufficiently soluble in a carrier, such as a plasticizer or other liquid processing aid, to be provided to the polymer resin through solution in the carrier alone. In such case, an organic solvent is used which is a cosolvent for the microbicidal compound and the carrier, e.g., the plasticizer. Specifically, the present invention is directed to applications in which the cosolvent is an organophosphite or organophosphonate, or mixtures thereof which have been found to allow the addition of relatively high levels of microbicidal compounds to a carrier, e.g., plasticizer, and provide homogeneous, stable compositions. More specifically, the present invention is directed to applications in which the cosolvent is an alkyl, aryl, alkyl-aryl, glycol, or thio- phosphite; or an alkyl, aryl, or alkyl-aryl phosphonate, or mixtures thereof which have been found to allow the addition of relatively high levels of microbicidal compounds to a carrier, e.g., plasticizer; and provide homogeneous, stable compositions. As used herein, the term "stable" means that the microbicide remains dissolved in the carrier-containing composition and does not precipitate or recrystallize after standing at room temperature for a period of about 30 days, or after being subjected to 5 freeze/thaw cycles.

The microbicidal phenoxarsines and phenarsazines useful in the compositions of this invention are represented by the following formulae:

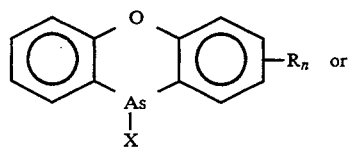

-continued

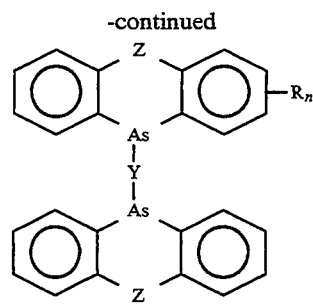

wherein X is halogen or thiocyanate, Y is oxygen or sulfur, Z is oxygen or nitrogen, R is halogen or lower alkyl, and n is 0 to 3. Representative phenoxarsines useful in the present invention are 10-chloro-phenoxarsine, 10-iodo-phenoxarsine, 10-bromophenoxarsine, 4-methyl- 10-chlorophenoxarsine, 2-tertiary butyl-10-chlorophenoxarsine, 1,4-dimethyl-10-chlorophenoxarsine, 2-methyl- 8,10-dichloro phenoxarsine, 1,3,10-trichloro phenoxarsine, 2,6,10-trichloro phenoxarsine, 2,8,10-trichloro phenoxarsine, 1,2,4,10-tetrachloro phenoxarsine, 10,10' oxybis phenoxarsine, 10-thiocyanato phenoxarsine or 10,10'-thio bis phenoxarsine. The preferred phenoxarsine is 10,10'-oxybis phenoxarsine.

The more preferred microbicidal compounds are the bisphenoxarsines and bisphenarsazines having the formula:

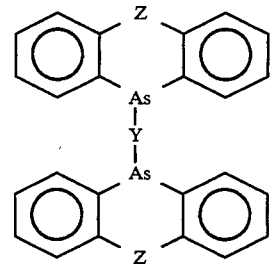

where Y is oxygen or sulfur and Z is oxygen or nitrogen. Of these bisphenoxarsines and bisphenarsazines, the most preferred are 10,10'-oxybisphenoxarsine; 10,10'-thiobisphenoxarsine; 10,10'-oxybisphenarsazine; and 10,10'-thiobisphenarsazine.

The microbicidal compositions useful in this invention should be employed in an amount at least sufficient to impart microbicidal properties to the polymer resin composition or material containing them. This amount can vary widely depending upon the particular microbicidal compound employed, the other components of the composition in which it is employed, the environment in which it will function and several other factors. The minimum amount of microbicidal compound employed with a particular polymer resin is determined by the amount of microbicide which demonstrates microbicidal activity against a particular microorganism (bacteria or fungus). A higher level of microbicide may be used to provide protection against a broader spectrum of microorganisms. The maximum amount of microbicidal compound which can be employed is determined only by the amount of microbicidal compound which can be uniformly incorporated into a particular composition without adversely affecting the physical properties of the composition. In general, the polymer resin compositions, treated with the microbicidal compositions of this invention, which possess microbicidal properties, contain from about 50 parts per million (ppm) to about 10,000 ppm, preferably about 100 ppm to 500 ppm, of microbicidal compound.

The liquid microbicidal/plasticizer solutions (hereinafter referred to as microbicidal solutions) of this invention preferably contain much more microbicidal compound than would be necessary simply to impart the desired microbicidal properties to them. For example, the liquid microbicidal solutions may contain from about 2.5 to about 15 weight percent microbicidal compound (based on the total weight of the microbicide, cosolvent, and plasticizer). More preferably the microbicidal solution would contain more than about 3.0 to about 10 weight percent microbicide in order to provide a microbicidal solution which can more easily be dispersed in a polymer resin. Most preferably the microbicidal solution should contain from more than about 3.5 to about 7.5 weight percent microbicide in order to provide a microbicidal solution which can be handled more safely. However, a solution containing, for example, 15% microbicidal compound may be used to prepare a polymer composition containing only 100 to 500 ppm microbicidal compound.

The organophosphite and organophosphonate cosolvents encompassed by the present invention include, but are not limited to, alkyl phosphites, such as diisooctyl phosphite, distearyl phosphite, triisodecyl phosphite, triisooctyl phosphite, trilauryl phosphite, tristearyl phosphite, and tris (dipropyleneglycol) phosphite; aryl phosphites, such as diphenyl phosphite, trisnonylphenyl phosphite, triphenyl phosphite; alkyl-aryl phosphites, such as, diphenyl isodecyl phosphite, diphenyl isooctyl phosphite, phenyl diisodecyl phosphite, poly 4, 4' isopropylidenediphenol neodol 25 phosphite; polyether phosphites such as the monophosphites, diphosphites and triphosphites; and thio-phosphites. The more preferred phosphites are aryl phosphites due to their improved performance.

In addition, suitable glycol phosphites for use with this invention include polyalkeneglycol phosphites such as tris (dipropyleneglycol) phosphite, tris (triethyleneglycol) phosphite, tetrakis (nonylphenyl) polypropyleneglycol diphosphite, bis(neopentyl-glycol) triethylenegylcyl diphosphite, heptakis (dipropyleneglycol) triphosphite, poly (dipropylene glycol-phenyl) phosphite, bis-dipropylene glycol isodecyl phosphite or the like. Representative suitable phosphonates include bis(dipropyleneglycol) dipropyleneglycol phosphonate or the like. The preferred glycol phosphites are tris (dipropyleneglycol) phosphite, poly (dipropylene glycol-phenyl) phosphite, bis (neopentylglycol) triethylene glycol diphosphite and tetrakis (nonylphenyl) polypropyleneglycol diphosphite. These phosphites and phosphonates also can be employed in combination. In some references the term glycyl was used to denote glycols. These phosphites and phosphonates are commercially available from a number of sources.

The phenoxarsine-organophosphite or phenoxarsine-organophosphonate compositions of this invention are admixed with plasticizers for the polymer resins into which the compositions are to be incorporated, which plasticizers normally are not solvents for the phenoxarsine compounds. It has been found that the compositions containing the plasticizers are compatible in that the phenoxarsine compounds do not precipitate or otherwise become separated from the other components in the composition. Therefore, substantial advantages are provided with these compositions since the plasticizer and the microbicidal compound can be incorporated with the resin in one mixing step. Examples of these plasticizers include, but are not limited to, typical plasticizers such as tricresyl phosphate, dipropylene glycol dibenzoate, diphenylcresyl phosphate, dipropylene glycol dibenzoate, diphenylcresyl phosphate, epoxidized soya, epoxidized tallate, dioctyl azelate, di(2-ethyl hexyl) phthalate, alkyl aryl phosphates, diisobutyl phthalate, diisodecyl phthalate, n-octyl n-decyl phthalate, mixed n-alkyl phthalates, butyl benzyl phthalate, di-n-octyl phthalate, di-n-decyl phthalate, 3,4-epoxycyclohexyl methyl 3,4-epoxycyclohexane carboxylate, trioctyl trimellitate and low molecular weight polymeric plasticizers, such as Paraplex G-30 plasticizer sold by Rohm & Haas Co. and the like. Of these plasticizers, di(2-ethyl hexyl) phthalate, diisodecyl phthalate, butyl benzyl phthalate and epoxidized soya are preferred. Other polymer processing aids useful in this invention include, but are not limited to, hydrogenated methyl rosin ester; polypropylene glycol; 1,2-butanediol; silicone oils such as polydimethylsiloxane; and methyl ethyl ketone.

The microbicidal solutions of this invention can be used in combination with UV stabilizers, antioxidants, and heat stabilizers used in polymer processing. Examples of UV stabilizers for use with this invention include, but are not limited to, UV screens and their synergists, such as carbon black, titanium dioxide, zinc oxide, zinc dialkyl dithiocarbamates (methyl and ethyl zimate), nickel organic salts, and phosphites; UV absorbers, such as, benzophenones, benzotriazoles, aryl esters, oxanilides, acrylic esters, and formamidines; and UV quenchers, such as, organic nickel compounds; and scavengers, such as, hindered amines. Examples of antioxidants for use with this invention include, but are not limited to, primary antioxidants, such as, hindered phenolics, and aromatic amines; and secondary antioxidants, such as, thioesters and phosphites. Examples of heat stabilizers for use with this invention include, but are not limited to, mixed metal soaps and organotin compounds.

As previously indicated, the concentration of microbicidal compound in the microbicidal solution of this invention will contain enough microbicidal compound that when added to a polymer resin composition the microbicidal solution will impart microbicidal properties to the polymer composition. It is in this aspect of the invention where the cosolvents employed in the practice of the present invention are particularly advantageous. The organophosphite or organophosphonate of this invention are capable of forming microbicidal solutions which produce compositions containing concentrations of microbicidal compounds significantly higher than could be achieved with prior art solvents. For example, heretofore OBPA-containing plasticizer compositions contained a maximum of about 2% by weight OBPA based on the weight of the plasticizing composition with a glycol phosphite as a cosolvent. It has now been quite unexpectedly found that the organophosphite or organophosphonate of this invention are capable of producing OBPA-containing plasticizing compositions containing up to about 15% by weight OBPA based on the weight of the microbicide, cosolvent, and plasticizer.

This unexpected ability of the organophosphite or organophosphonate to produce plasticizer-containing compositions containing high levels of microbicidal compound leads to several very significant advantages. For example, shipping and handling cost savings are achieved because more "active ingredient" (the microbicidal compound) can now be dissolved in a given amount of plasticizer-containing composition. Stated another way, for a given amount of microbicidal compound, less "inert ingredients" (solvent and plasticizer) are required to produce a plasticizer-containing composition, resulting in raw material cost savings. Also, because less inert ingredients are needed, handling and shipping costs are lower. These advantages must be balanced against the inherent toxicity of the microbicidal solutions of this invention and the ease of dispersing the microbicidal solutions in the polymer resin.

The microbicidal solutions of this invention also minimize the potential effects of the plasticizer on polymer formulations containing them. Because less plasticizer is required to prepare a microbicide composition/plasticizer containing a given level of microbicidal compound, less plasticizer is introduced into the polymer formulation. Therefore, if the plasticizer is not entirely compatible with the other components of the polymer formulation, the negative effects of that incompatibility will be minimized.

The polymers employed in the processes and products of this invention cover a wide variety of materials. In general, they include thermoplastic and thermosetting polymers, elastomers and other materials commonly known as "plastics". Other organic materials, for instance naturally occurring materials such as natural rubbers, cellulose and the like are considered full equivalents of the "polymers" of this invention and should be included within that term. Examples of the polymers useful in the practice of this invention include, but are not limited to vinyl resins (such as those made from vinyl chloride and/or vinyl esters) polyolefins (such as polyethylene and polypropylene), elastomeric polyurethanes, nylon, polystyrene, polyesters (such as polyethylene terephthalate), polycarbonates, acrylonitrile-butadiene-styrene (ABS) copolymers, SBR rubbers, styrene-acrylonitrile copolymers, acrylic polymers, thermosetting polyurethanes (such as those used for foams and coatings), phenolic resins, silicone rubbers, natural rubber, EDPM polymers, cellulose and its derivatives, epoxy resins and various latexes.

The microbicidal solutions of this invention can be prepared by simply adding the desired amount of microbicidal compound to the organophosphite, organophosphonate, glycol phosphite, or glycol phosphonate cosolvent, heating the resulting mixture to a temperature which will cause the microbicidal compound to dissolve, and maintaining that temperature until all of the microbicidal compound dissolves. The resulting solution can then be cooled to room temperature. In this manner, stable microbicidal solutions, i.e. those wherein no significant amount of microbicidal compound precipitates from the solution upon cooling to room temperature, can be formed containing up to about 50% by weight microbicidal compound based on the weight of the resulting microbicidal solution. The plasticizer-containing compositions of the present invention may be prepared by merely adding the plasticizer to a microbicidal solution prepared as described above and mixing at room temperature until a uniform solution results. Alternatively, all ingredients of the plasticizer-containing composition (microbicidal compound, organophosphite or organophosphonate and plasticizer) can be mixed together and heated until the microbicidal compound dissolves.

The microbicide solutions of this invention can be used to impart microbicidal properties to polymer compositions. This can be done by simply adding microbicidal solution of this invention to the polymer composition by any of several convenient methods known in the art. Thus, for instance, the polymer composition can be melted and the microbicidal solutions added to and mixed with it (as in an extruder). Alternatively, the polymer can be softened with or dissolved in a solvent and the microbicidal solutions added to and mixed therewith.

The following examples illustrate the present invention and are not intended to limit the invention or its scope in any manner. As used in the examples and throughout this specification, all parts and percentages are by weight unless otherwise indicated.

EXAMPLE I

Compositions containing 20 wt.% 10,10'-oxybis phenoxarsine (OBPA) and 80 wt. % Diphenyl isooctyl phosphite (Weston ODPP or Mark C), Trisnonylphenyl Phosphite (WESTON TNPP), and Tris(dipropyleneglycol) Phosphite (WESTON 430), respectively, were prepared by first mixing the 80 g 10,10'-oxybis phenoxarsine (OBPA) with 320 g of the organophosphite. The resultant mixture was then agitated while being heated until the OBPA dissolved. The mixtures were heated from 5° to 30° above the temperature required to achieve solution. The Mark C solution was heated to 225° F. The Weston TNPP solution was heated to 350° F. The WESTON 430 solution was heated to 250° F. The solutions then were allowed to cool slightly before being diluted or "let down" with the plasticizer.

As set forth in following table the mixtures of OBPA and the organophosphites were diluted or "let down" using diisodecyl phthalate (DIDP), butyl benzyl phthalate (S-160) and epoxidized soya (ESO). The OBPA-organophosphite solutions were added to the plasticizer at room temperature and agitated to insure uniform mixture.

| | PLASTICIZER COMPOSITION wt. % | | | | | | | | |
|---|---|---|---|---|---|---|---|---|---|
| | 1 | 2 | 3 | 4 | 5 | 6 | 7 | 8 | 9 |
| Mark C | | | | | 20 | 40 | 60 | | |
| Trisnonylphenyl Phosphite (WESTON TNPP) | | | | | | | | 20 | 40 |
| Tris(dipropyleneglycol) Phosphite (WESTON 430) | 8 | 8 | 8 | 20 | | | | | |
| 10,10'-oxybis phenoxarsine (OBPA) | 2 | 2 | 2 | 5 | 5 | 10 | 15 | 5 | 10 |
| Diisodecyl Phthalate | 90 | | | | 75 | 50 | 25 | 75 | 50 |
| BUTYL BENZYL PHTHALATE S-160 | | 90 | | 75 | | | | | |
| Epoxidized Soya | | | 90 | | | | | | |
| Solubility | | | | | | | | | |
| (Room Temp.) | S | S | S | S | S | S | S | S | S |
| (Freeze/Thaw) | | | | | S | S | S | S | S |

| | PHOSPHITES wt. % | | | | | | | | |
|---|---|---|---|---|---|---|---|---|---|
| | 10 | 11 | 12 | 13 | 14 | 15 | 16 | 17 | 18 |
| Mark C | | | | | 20 | 40 | 60 | | |
| Trisnonylphenyl Phosphite (WESTON TNPP) | 60 | | | | | | | 20 | 40 |
| Tris(dipropyleneglycol) Phosphite (WESTON | | 20 | 40 | 60 | | | | | |

-continued

| | | | | | | | | | |
|---|---|---|---|---|---|---|---|---|---|
| 430) | | | | | | | | | |
| 10,10'-oxybis phenoxarsine (OBPA) | 15 | 5 | 10 | 15 | 5 | 10 | 15 | 5 | 10 |
| Diisodecyl Phthalate | 25 | 75 | 50 | 25 | | | | | |
| BUTYL BENZYL PHTHALATE S-160 | | | | | | | | | |
| Epoxidized Soya | | | | | 75 | 50 | 25 | 75 | 50 |
| Solubility | | | | | | | | | |
| (Room Temp.) | S | S | S | TP | S | S | S | S | S |
| (Freeze/Thaw) | S | S | S | MP | S | S | TP | S | S |

| | PHOSPHITES wt. % | | | |
|---|---|---|---|---|
| | 19 | 20 | 21 | 22 |
| Mark C | | | | |
| Trisnonylphenyl Phosphite (WESTON TNPP) | 60 | | | |
| Tris(dipropyleneglycol) Phosphite (WESTON 430) | | 20 | 40 | 60 |
| 10,10'-oxybis phenoxarsine (OBPA) | 15 | 5 | 10 | 15 |
| Diisodecyl Phthalate | | | | |
| BUTYL BENZYL PHTHALATE S-160 | | | | |
| Epoxidized Soya | 25 | 75 | 50 | 25 |
| Solubility | | | | |
| (Room Temp.) | S | S | S | TP |
| (Freeze/Thaw) | S | S | S | S |

S = Soluble
TP = Trace Precipitate
MP = Moderate Precipitate

Thereafter, the solutions were immediately separated into two samples, one sample for room temperature aging and one sample for freeze/thaw aging. Thereafter, each freeze/thaw sample was subjected to a freeze-thaw cycle at 0° F. for two days and room temperature for one day on a continuous basis for five cycles.

A slight sediment or "foots" appeared in the ESO samples, which is due to the plasticizer. All of the solutions prepared with Weston TNPP were stable and showed no signs of precipitation. The plasticizer solutions of 5% and 10% OBPA made with Weston 430 were stable. The 15% OBPA solution in ESO made with Weston 430 passed the freeze-thaw cycling but a few crystals developed in the room temperature samples. The 15% OBPA solution in DIDP with Mark C became hazy over time. It is believed that these samples would be useable commercially at an OBPA concentration slightly less than 15%. The 15% OBPA solution in DIDP with Weston 430 had a slight amount of precipitate in the room temperature sample and moderate amount of precipitate in the freeze-thaw sample.

We claim:

1. A stable liquid microbicidal composition comprising a plasticizer, a microbicidal compound, and a cosolvent, wherein from about 2.5% to about 15%, based on the total weight of the liquid microbicidal composition, of said microbicidal compound is present in the stable liquid microbicidal composition wherein said microbicidal compound is selected from the group consisting of phenoxarsines and phenarsazines, said microbicidal compound being present as the solute in an organophosphite cosolvent or organophosphonate cosolvent such that the weight ratio of the organophosphite or organophosphonate cosolvent to microbicidal compound is from about 1/1 to about 5/1; and wherein said plasticizer is selected from the group consisting of tricresyl phosphate, dipropylene glycol dibenzoate, diphenylcresyl phosphate, dipropylene glycol dibenzoate, diphenylcresyl phosphate, epoxidized soya, epoxidized tallate, dioctyl azelate, di(2-ethyl hexyl) phthalate, alkyl aryl phosphates, diisobutyl phthalate, diisodecyl phthalate, n-octyl n-decyl phthalate, mixed n-alkyl phthalates, butyl benzyl phthalate, di-n-octyl phthalate, di-n-decyl phthalate, 3,4-epoxycyclohexyl methyl 3,4-epoxycyclohexane carboxylate, and trioctyl trimellitate.

2. The stable liquid microbicidal composition of claim 1 comprising a plasticizer, and from about 2.5% to about 15% by weight, based on the total weight of the liquid microbicidal composition, of a microbicidal compound selected from the group consisting of phenoxarsines and phenarsazines, said microbicidal compound being present as the solute in an aryl phosphite or aryl phosphonate such that the weight ratio of the aryl phosphite or aryl phosphonate cosolvent to microbicidal compound is from about 1/1 to about 5/1.

3. The stable liquid microbicidal composition of claim 1 comprising a plasticizer, and from about 2.5% to about 15% by weight, based on the total weight of the liquid microbicidal composition, of a microbicidal compound selected from the group consisting of phenoxarsines and phenarsazines, said microbicidal compound being present as the solute in an alkyl phosphite or alkyl phosphonate such that the weight ratio of the alkyl phosphite or alkyl phosphonate cosolvent to microbicidal compound is from about 1/1 to about 5/1.

4. The stable liquid microbicidal composition of claim 1 comprising a plasticizer, and from about 2.5% to about 15% by weight, based on the total weight of the liquid microbicidal composition, of a microbicidal compound selected from the group consisting of phenoxarsines and phenarsazines, said microbicidal compound being present as the solute in an alkyl-aryl phosphite or alkyl-aryl phosphonate such that the weight ratio of the alkyl-aryl phosphite or alkyl-aryl phosphonate cosolvent to microbicidal compound is from about 1/1 to about 5/1.

5. The stable liquid microbicidal composition of claim 1 comprising a plasticizer, and from about 2.5% to about 10% by weight, based on the total weight of the liquid microbicidal composition, of a microbicidal compound selected from the group consisting of phenoxarsines and phenarsazines, said microbicidal compound being present as the solute in an glycol phosphite or glycol phosphonate such that the weight ratio of the glycol phosphite or glycol phosphonate cosolvent to microbicidal compound is from about 1/1 to about 5/1.

6. The stable liquid microbicidal composition of claim 1 wherein the phenoxarsine compound is of the formula selected from the group consisting of

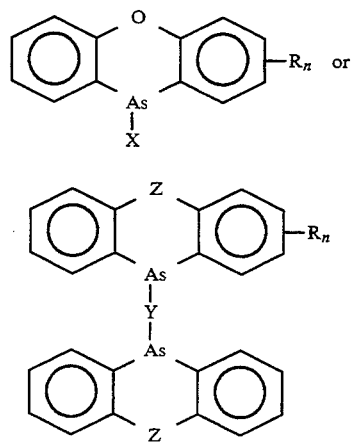

wherein X is halogen or thiocyanate, Y is oxygen or sulfur, Z is oxygen or nitrogen, R is halogen or lower alkyl, and n is 0 to 3.

7. The stable liquid microbicidal composition of claim 1 wherein the weight ratio of the organophosphite or organophosphonate cosolvent to microbicidal compound is from about 3/1 to about 5/1.

8. The stable liquid microbicidal composition of claim 1 wherein the organophosphite is tris (dipropyleneglycol) phosphite.

9. The stable liquid microbicidal composition of claim 1 wherein the organophosphite is trisnonylphenyl phosphite.

10. The stable liquid microbicidal composition of claim 1 wherein the microbicidal compound is selected form the group consisting of 10, 10' -oxybisphenoxarsine; 10,10'-thiobisphenoxasine; 10,10'-oxbisphenarsazine; and 10,10'-thiobisphenarsazine.

11. The stable liquid microbicidal composition of claim 2 wherein the microbicidal compound is 10,10'-oxybisphenoxarsine.

12. The stable liquid microbicidal composition of claim 1 further comprising a UV stabilizer.

13. The stable liquid microbicidal composition of claim 1 further comprising an antioxidant.

14. The stable liquid microbicidal composition of claim 1 further comprising a heat stabilizer.

* * * * *